United States Patent [19]
Szlosek

[11] Patent Number: 6,033,605
[45] Date of Patent: Mar. 7, 2000

[54] MICROPLATES WHICH PREVENT OPTICAL CROSS-TALK BETWEEN WELLS

[75] Inventor: Paul M. Szlosek, Kennebunk, Me.

[73] Assignee: Corning Incorporated, Corning, N.Y.

[21] Appl. No.: 09/016,158

[22] Filed: Jan. 30, 1998

Related U.S. Application Data

[62] Division of application No. 08/539,421, Oct. 5, 1995, Pat. No. 5,759,494.

[51] Int. Cl.[7] .............................. B29D 11/00; B01L 3/00
[52] U.S. Cl. ........................... 264/1.7; 264/2.5; 264/274; 264/279; 422/102
[58] Field of Search ............................ 264/1.7, 2.5, 274, 264/279, 279.1; 422/99, 101, 102; 356/256, 440

[56] References Cited

U.S. PATENT DOCUMENTS

| | | |
|---|---|---|
| 4,154,795 | 5/1979 | Thorne . |
| 4,431,307 | 2/1984 | Suovaniemi . |
| 4,510,119 | 4/1985 | Hevey . |
| 4,948,442 | 8/1990 | Manns . |
| 5,047,215 | 9/1991 | Manns . |
| 5,082,628 | 1/1992 | Andreotti et al. . |
| 5,225,164 | 7/1993 | Astle ....................................... 422/102 |
| 5,298,753 | 3/1994 | Sonne et al. . |
| 5,307,144 | 4/1994 | Hiroshi et al. ........................... 422/102 |
| 5,319,436 | 6/1994 | Manns et al. . |
| 5,457,527 | 10/1995 | Manns et al. . |
| 5,487,872 | 1/1996 | Hafeman et al. ........................ 422/102 |

FOREIGN PATENT DOCUMENTS

| | | |
|---|---|---|
| 0 329 120 | 8/1989 | European Pat. Off. . |
| 44 12 893 A1 | 10/1995 | Germany . |
| 07020037 | 1/1995 | Japan . |

*Primary Examiner*—Mathieu D. Vargot
*Attorney, Agent, or Firm*—Wolf, Greenfield & Sacks, P.C.

[57] ABSTRACT

A microplate and a method for manufacturing microplates. The microplate is designed to reduce optical cross-talk during the assaying of samples. The microplate includes a plurality of wells having light permeable sidewalls, a layer of light permeable material forming a bottom of the wells, and ribs of light impermeable material extending through the layer of light permeable material. The method includes steps of inserting a plate of light permeable material into a mold cavity that includes sections shaped to form the sidewalls of the plurality of wells, injecting molten light impermeable material into the mold cavity, and cooling the light impermeable material to form the microplate with the light impermeable material forming the sidewalls of each of the plurality of wells and the plate of light permeable material forming the bottom wall of each of the plurality of wells.

17 Claims, 4 Drawing Sheets

6,033,605

MICROPLATES WHICH PREVENT OPTICAL CROSS-TALK BETWEEN WELLS

This application is a divisional of application Ser. No. 08/539,421, filed Oct. 5, 1995, entitled MICROPLATES WHICH PREVENT OPTICAL CROSS-TALK BETWEEN WELLS, and now U.S. Pat. No. 5,759,494.

FIELD OF THE INVENTION

The present invention relates generally to microplates, and more specifically to microplates that prevent optical cross-talk between wells when used to assay samples.

BACKGROUND OF THE INVENTION

Assays of chemical reactions, utilizing techniques such as, for example, scintillation counting, luminometry, fluorimetry and kinetics measurements, are carried out on a large scale in both industry and academia. As a result, it is desirable to have an apparatus that allows such assays to be performed in a convenient and inexpensive fashion.

Because they are relatively easy to handle and low in cost, microplates are commonly used for performing assays of chemical reactions. Microplates typically consist of a plurality of individual wells. An aliquot of a sample to be assayed is placed in each well. The wells are usually arranged in relatively close proximity in a matrix pattern. Common sizes for microplates include matrices having dimensions of 4×6 (24 wells) or 8×12 (96 wells), although larger microplates are also used that may include matrices of hundreds or even thousands of wells. Microplates are preferably arranged to allow each sample to be assayed independently of the other samples.

In certain assay methods frequently performed in wells (e.g, chemiluminescence), a chemical reaction is measured by the emission of visible light. Similarly, in assay methods such as fluorimetry, visible light is emitted when a sample is exposed to a specific wavelength of radiation to commence the chemical reaction. When performing assay methods involving the measurement of visible light from the samples, optical cross-talk may occur between microplate wells. Optical cross-talk is an interference in signal measurement that results from the transmission of photons of visible light between wells. Thus, the result measured from a particular well may be skewed by light emitted from a different sample. Therefore, optical cross-talk should be minimized because it negatively impacts the ability to assay samples individually.

Despite the harmful effects of optical cross-talk on the data produced by these assay methods, there exist relatively few microplates designed to significantly reduce this effect. It has been recognized that to reduce optical cross-talk between the wells of a microplate, certain regions of the wells such as the sidewalls should Be formed from material that does not allow the transmission of visible light therethrough. However, since light measurements are typically taken from the bottom surface of the wells, the bottom surface must generally be formed from a material that is transparent to visible light. Thus, optical cross-talk can occur through the transparent material that forms the bottom surfaces of the wells.

One attempt to reduce optical cross-talk in microplate wells is disclosed in U.S. Pat. No. 5,298,753 to Sonne et al, which discloses a microplate having wells that include a light permeable bottom plate and light impermeable sidewalls. To reduce the problem of optical cross-talk between adjacent wells, the lower surface of the bottom plate is provided with an adhesive tape having a grid of black lines positioned beneath the areas where the bottom. sheet contacts the light impermeable sidewalls. The black lines are said to reduce optical cross-talk by blocking some light rays that would otherwise pass between adjacent wells. However, because the adhesive tape is attached to the lower surface of the bottom plate, it necessarily cannot prevent the exchange of light between adjacent wells through the layer of material that forms the bottom layer. Therefore, Sonne concedes that the disclosed technique is only 90% effective in reducing optical cross-talk. Furthermore, given the laboratory environment in which this microplate is likely to be used, the adhesive may not be sufficiently durable to withstand repeated use.

Another example of a microplate designed to reduce optical cross-talk is disclosed in U.S. Pat. No. 5,319,436 to Manns et al. This microplate also includes an opaque upper plate that forms sidewalls for each well, and a transparent lower plate. The upper and lower plates have relatively complex designs so that they may be mated together and sonically bonded to form the microplate. The opaque material includes a bead surrounding each well, and extending partially into the transparent lower plate. It is said that the opaque beads should extend through 25–75% of the thickness of the lower plate, and that they provide a barrier to light transmission between adjacent wells. However, because the beads do not extend entirely through the transparent lower plate, light transmission between adjacent wells through the bottom plate is not completely eliminated. Furthermore, the relatively intricate designs of the upper and lower plates that must be mated together and sonically bonded result in a comparatively expensive manufacturing process.

It is an object of the present invention to provide an improved microplate for use in assaying samples and an improved method for manufacturing microplates.

SUMMARY OF THE INVENTION

In one illustrative embodiment of the invention, a microplate is provided that comprises a plurality of wells including at least first and second wells, a layer of light permeable material that forms a bottom of at least the first and second wells, and at least one rib of light impermeable material extending entirely through the layer of light permeable material, the at least one rib being disposed between the first and second wells to prevent light from passing between the first and second wells through the light permeable material.

In another illustrative embodiment of the invention, a microplate is provided that comprises a frame including a plurality of wells, a light permeable plate forming a bottom of each of the plurality of wells, and means for preventing light from passing between adjacent ones of the plurality of wells through the light permeable plate.

In a further illustrative embodiment of the invention, a microplate is provided that comprises a plurality of wells including at least first and second wells having light impermeable sidewalls, a layer of light permeable material that forms a bottom of each of the first and second wells, the layer of light permeable material having a thickness, and at least one rib of light impermeable material extending through greater than 75% of the thickness of the layer of light permeable material, the at least one rib being disposed between the first and second wells.

In another illustrative embodiment of the invention, a microplate is provided that comprises a plurality of wells including at least first and second wells, the first and second wells each having light impermeable sidewalls and a light permeable bottom, and at least one rib of light impermeable material disposed between the bottoms of the first and second wells so that any plane passing through the bottom of the first well and the bottom of the second well intersects the at least one rib.

In a further illustrative embodiment of the invention, a method is provided for making a microplate having a plurality of wells, each of the plurality of wells having light impermeable sidewalls and a light permeable bottom wall. The method comprises the steps of: (A) inserting a plate of light permeable material into a mold cavity that includes sections shaped to form the sidewalls of the plurality of wells, the plate being positioned adjacent the sections shaped to form the sidewalls of the plurality of wells in a location corresponding to the bottom walls of the plurality of wells; (B) injecting molten light impermeable material into the mold cavity; and (C) cooling the light impermeable material to form the microplate with the light impermeable material forming the sidewalls of each of the plurality of wells and the plate of light permeable material forming the bottom wall of each of the plurality of wells.

These and other objects and features of the present invention will be better understood and appreciated from the following detailed description of several illustrative embodiments of the invention and the accompanying drawings.

DETAILED DESCRIPTION OF THE INVENTION

Figure 1:
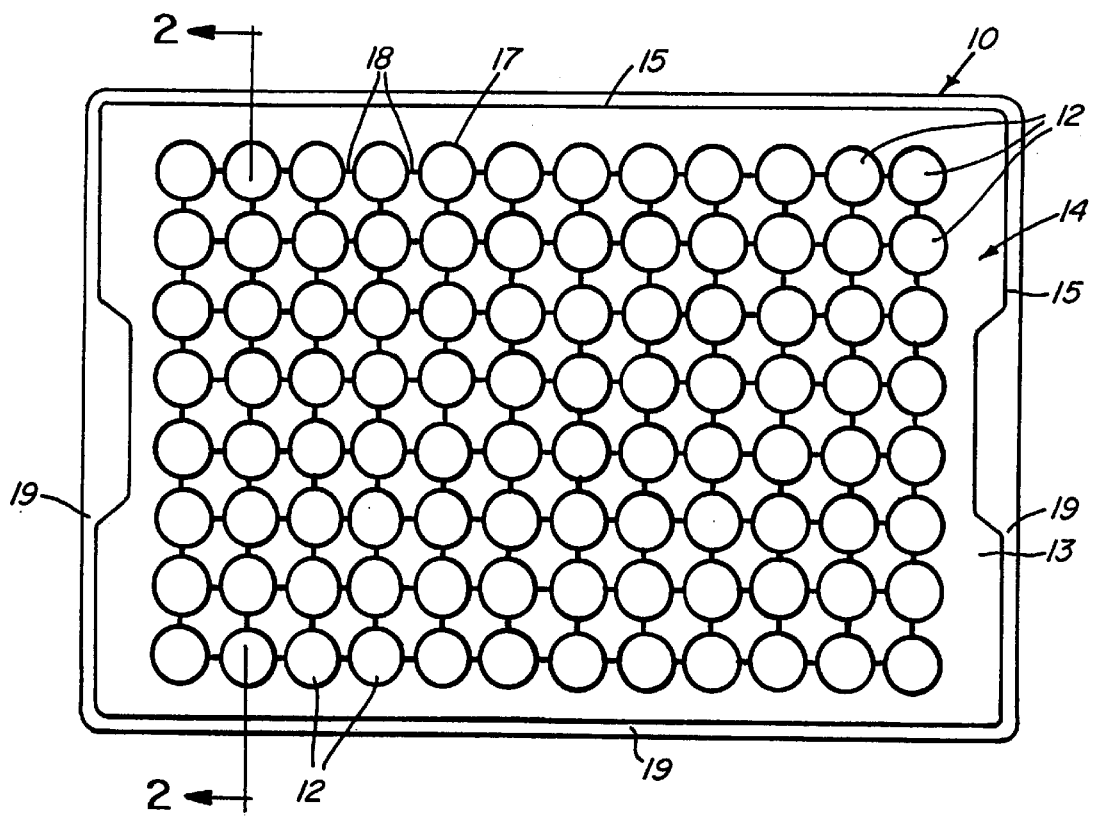
FIG. 1 is a top view of a microplate in accordance with the present invention.
Figure 2:
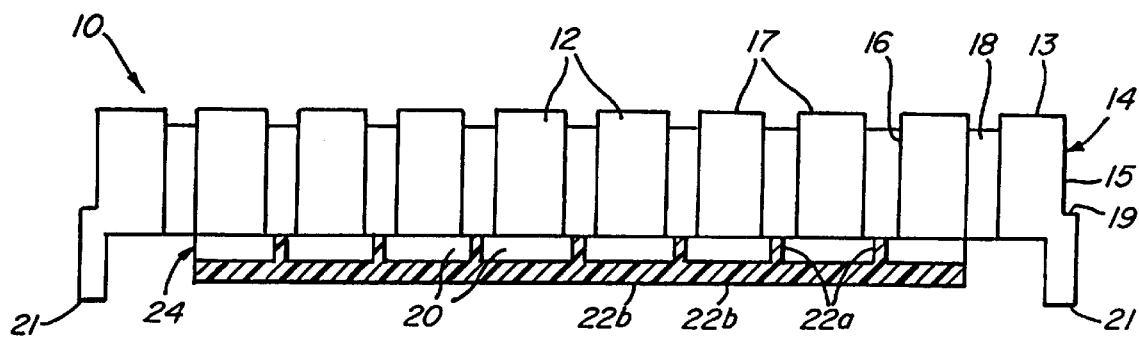
FIG. 2 is a fragmentary cross-sectional view of the microplate of FIG. 1 taken along the section line 2—2 in FIG. 1.
Figure 3:
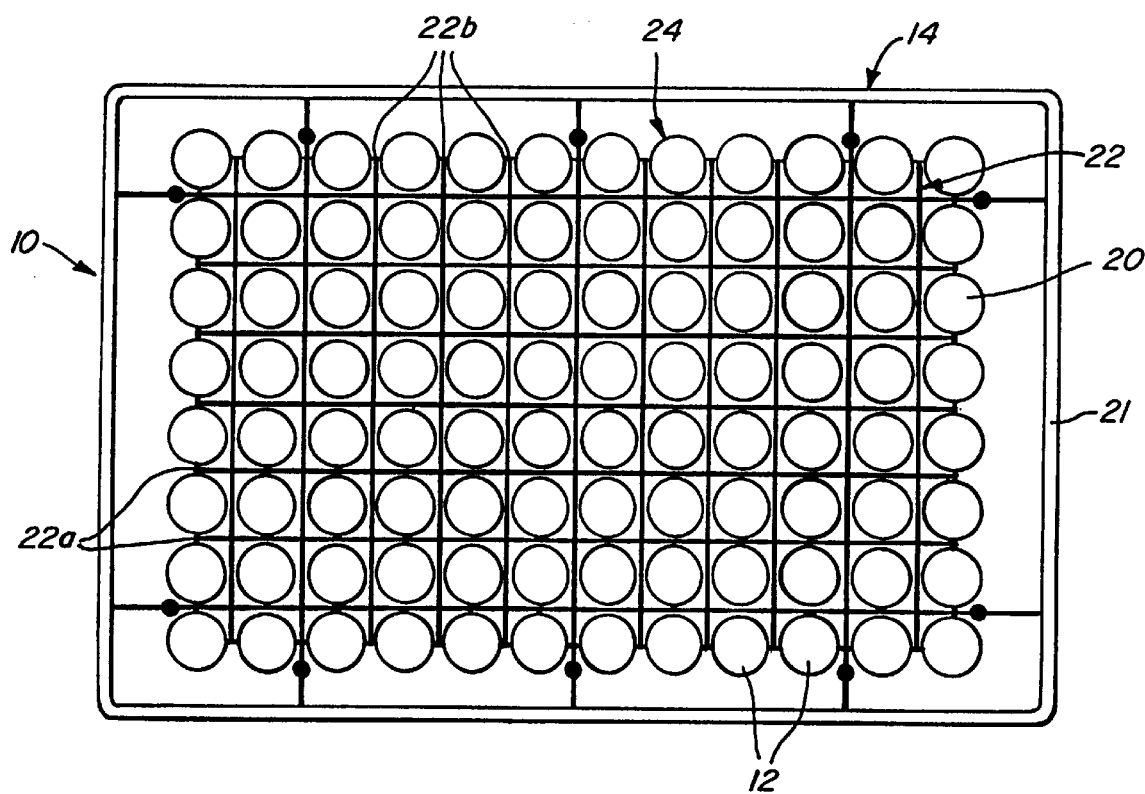
FIG. 3 is a bottom view of the microplate of FIGS. 1–2.

An illustrative microplate 10 in accordance with the present invention is shown in FIGS. 1–3, with FIG. 1 being a top view, FIG. 2 a cross-sectional view along line 2—2 of FIG. 1, and FIG. 3 a bottom view. The microplate 10 includes an array of wells 12, each of which may receive an aliquot of a sample to be assayed. In the embodiment shown, the microplate includes ninety-six wells arranged in a grid having a plurality of rows and columns. However, the present invention is not limited to this arrangement. The present invention can be implemented in any type of microplate arrangement, including all established industry standards (e.g., six, twenty-four, forty-eight, ninety-six, or more wells), and is not limited to any specific number of wells or any specific plate dimensions.

Each well includes a top rim 17, sidewalls 16 (FIG. 2) and a bottom 20 (FIG. 3). The top rim 17 and sidewalls 16 are formed from a light impermeable material, and the bottom 20 from a light permeable material. As seen from the top view of FIG. 1, the microplate includes a frame 14 that supports the wells 12. Frame 14 includes outer walls 15 and a top planar surface 13 extending between the outer walls and the welts 12. In the embodiment shown, the frame is rectangular in shape. However, it should be understood that the frame 14 can be provided in any number of other geometrical shapes (e.g., triangular or square) depending on the desired arrangement of the wells 12. Support walls 18 connect the sidewalls 16 of adjacent wells, as shown in FIGS. 1–2. In the illustrative embodiment shown, the wells 12 have circular crosssections in a plane parallel to the planar surface 13. However, the invention is not limited in this respect, and it should be understood that wells 12 may be provided in a number of alternate configurations having different cross-sectional shapes, e.g., rectangles, squares and triangles.

In one embodiment of the invention, the outer wall 15 that defines the outer periphery of the frame 14 extends below the bottoms 20 of the wells. As shown in FIG. 2, the outer wall 15 has a bottom edge 21 that extends below the bottom 20 of the wells, so that when placed on a support surface, the microplate is supported by the bottom edges 21 with the well bottoms 20 being raised above the support surface to protect them from damage. In the configuration shown in FIGS. 1–3, each outer wall 15 also has a rim 19 to accommodate the skirt of a microplate cover (not shown).

Figure 4:
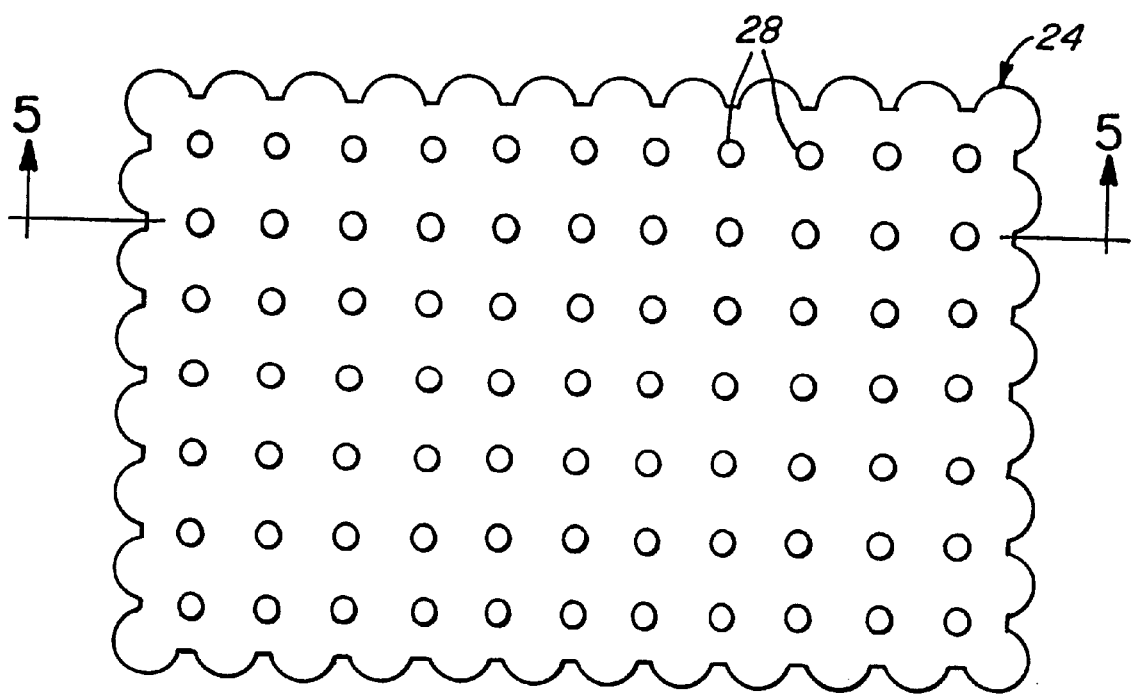
FIG. 4 is a top view of a light permeable plate that is inserted into a mold during molding of the microplate of the present invention and forms the bottom of each microplate well.

The bottoms 20 of the microplate wells 12 are formed from a single baseplate 24 of light permeable material. The baseplate 24 may be rectangular, scalloped along the outer edges as shown in FIG. 4 to conform to the arrangement of the array of wells, or any other shape that is suitable for establishing the bottom 20 of each well.

The microplate 10 is provided with a plurality of ribs 22 (FIGS. 2–3) that are formed from a light impermeable material. Each of the ribs 22 is contiguous with the sidewalls of the plurality of wells, is formed of the same light impermeable material, and extends entirely through the baseplate 24. In the embodiment shown in FIGS. 1–3, the ribs 22 are oriented in a grid arrangement with some of the ribs 22a extending in rows parallel to the length of the microplate, and others 22b extending in columns perpendicular to the length of the microplate. The ribs separate the baseplate 24 of light permeable material into separate compartments, with one well bottom 20 being enclosed in each compartment. Thus, light transmission from one well to another through the light permeable baseplate 24 is effectively prevented. As a result, optical cross-talk is limited to the minimal amount of light that passes through the light impermeable ribs.

In the embodiment shown in FIG. 3, the ribs are formed in the grid pattern because this arrangement is simple and economical to manufacture. However, it should be understood that the present invention is not limited to any particular rib arrangement, and that other arrangements can also be used. The present invention can employ any arrangement wherein adjacent well bottoms are separated by light impermeable ribs that extend through the layer of light permeable material to interfere with the transmission of visible light from one well bottom to another.

Although the ribs preferably pass entirely through the thickness of the light permeable layer that forms the well bottoms, other embodiments of the invention can be employed wherein the ribs extend only substantially through the thickness of that layer. In this respect, performance improvements over the prior art are achieved so long as the light impermeable ribs extend through greater than 75% of the thickness of the light permeable layer, thereby blocking a substantial amount of the optical cross-talk that would otherwise occur between adjacent wells.

As discussed above, the microplate 10 of the present invention is comprised of at least two materials. The baseplate 24 that forms the well bottoms 20 is made of a light permeable material. As used herein, the term light permeable is intended to identify a material that allows visible light to pass through with a reduction in intensity of not more than approximately 1.0%. Examples of light permeable materials suitable for use in the present invention include clear polystyrene, polyacrylonitrile, polycarbonate, polyolefin, polyester, polymethylpentene, and acrylic materials.

The remainder of the microplate, including frame 14, top well rims 17, well sidewalls 16, support walls 18, and ribs 22, is made of a light impermeable material. As used herein, ight impermeable denotes a material that allows no more than approximately 0.1% visible light transmission therethrough. In one embodiment of the invention, the light impermeable material reflects visible light and has a high albedo. Such a material may be formed by adding solid pigments that reflect light (e.g., titanium dioxide, zinc oxide, zinc sulfide and thiopene) to any of the plastic materials discussed above as being appropriate for forming the light permeable layer. Alternatively, a material that absorbs visible light can be selected for use as the light impermeable material, and can be formed by adding a solid pigment that absorbs light (e.g., carbon black) to any of the plastic materials listed above.

The microplate of the present invention can be made using any of a number of standard molding techniques, e.g., injection molding, extrusion, calendering and injection compression. Thus, the light impermeable and light permeable materials used in forming the microplate of the present invention are preferably moldable plastic materials, i.e., plastics that may be used with standard molding techniques. As used herein, the term plastic material denotes a material comprising a polymerization product incorporating repeating monomer units. In one embodiment of the invention, the specific plastics used are selected to be compatible with the particular assay method in which the microplate will be used. For example, the light permeable and impermeable materials can each be selected to be non-reactive or impervious with the components of the samples to be assayed. Similarly, the materials can be selected to be impervious to radiation or heating conditions to which the microplate is exposed during the course of an assay method.

Figure 5:
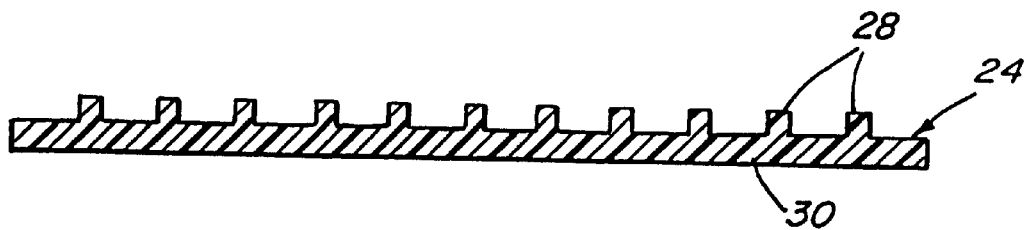
FIG. 5 is a cross-sectional view of the plate of FIG. 4 taken along the section line 5—5 in FIG. 4.
Figure 6:
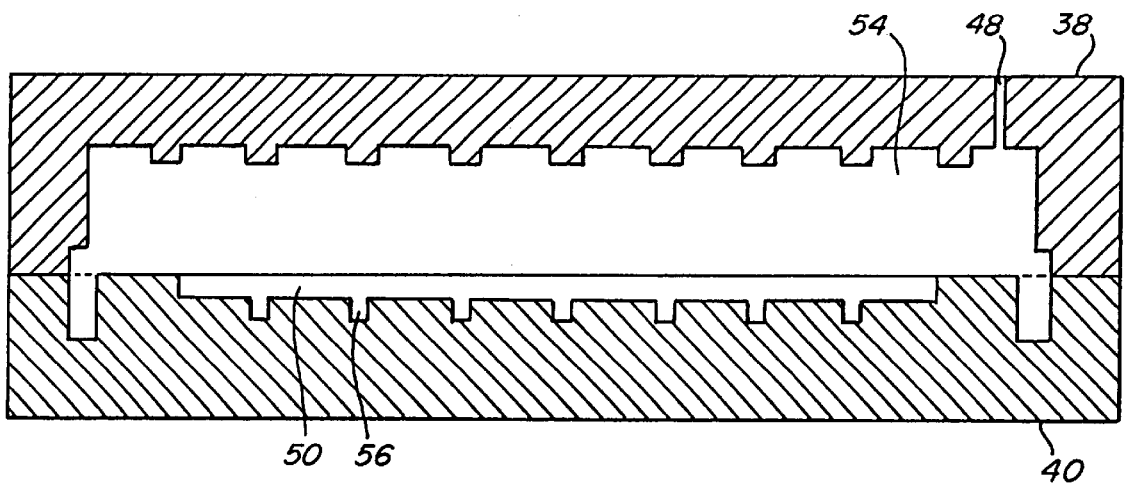
FIG. 6 is a fragmentary cross-sectional view of the mold and mold cavity in which the microplate of the present invention is formed.
Figure 7:
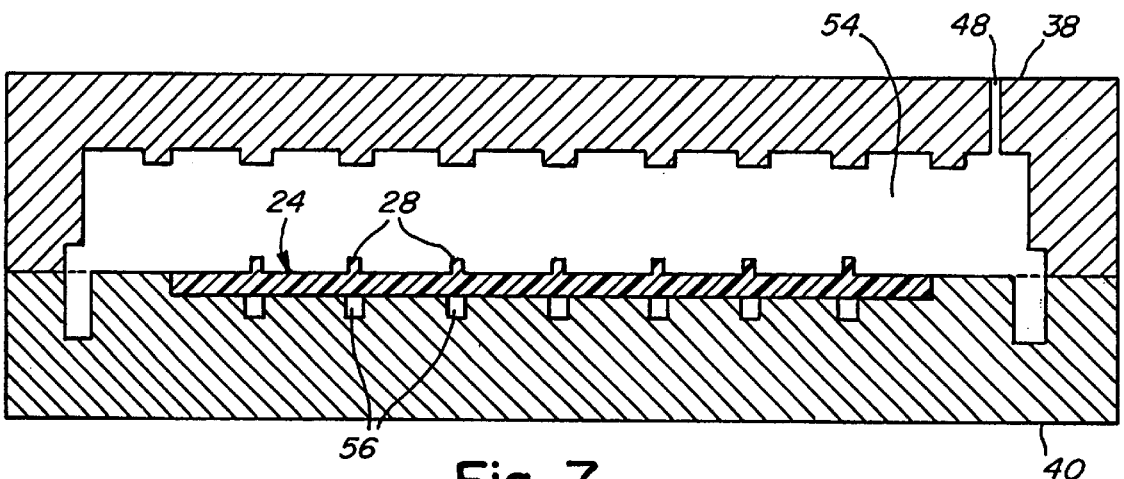
FIG. 7 is a fragmentary cross-sectional view similar to FIG. 6, but showing the plate of FIGS. 4–5 positioned in the mold cavity.

A method of forming a microplate in accordance with the present invention is described making reference to FIGS. 5–7. Initially, the baseplate 24 of light permeable material is formed using a standard molding technique, such as any of the ones listed above. As discussed above, the baseplate 24 may take any of a variety of geometrical shapes. In the cross-sectional view shown in FIG. 5, the rectangular baseplate 24 is illustrated as having a planar platform 30 and a plurality of nubs 28 extending therefrom. The purpose of the nubs is discussed below.

In molding the remainder of the microplate, a two-piece mold can be used having a well-mold piece 38 and a rib-mold piece 40 as shown in FIG. 6. The baseplate 24 that will ultimately form the well bottoms 20 is inserted into the cavity 50 of the rib-mold piece 40 shown in FIG. 7. The well-mold piece 38 is then mated with the rib-mold piece 40, enclosing the baseplate 24 therebetween. The two mold pieces form a chamber 54 that has a shape that conforms to the final shape of the microplate IO. The rib-mold piece 40 includes channels 56 that define the regions where the ribs 22 will be formed. Similarly, the portion of the chamber 54 defined by the well-mold piece 38 includes sections that define the shape of the frame 14, well sidewalls 16, support walls 18 and the remaining portions of the microplate that are disposed on the opposite side of the baseplate 24 from the ribs 22. It should be understood that alternate arrangements of the rib-mold and well-mold pieces can also be employed that would also enable the formation of the microplate having the desired configuration.

The baseplate 24 is positioned in the mold cavity 54, in a location corresponding to the bottom walls of the wells, with nubs 28 extending away from the rib-mold piece 40 and toward the well-mold piece 38. Baseplate 24 is positioned so that one of the nubs 28 is disposed at each row/column intersection of channels 56, which correspond to locations where the rows and columns of ribs 22 will intersect. The baseplate 24 separates the mold cavity 54 into multiple chambers, with one for each of the channels 56 that define the ribs 22, and one for the section of the mold cavity defined by the well-mold piece 38. The light impermeable material is then injected in a molten state at high pressure and high temperature into the chamber 54 through an injection port 48 in the well-mold piece 38. The mold cavity 54 does not provide any path for the molten material to pass from the sections of the cavity formed by the well-mold piece 38 into the channels 56, except through the baseplate 24. Upon injection into the chamber 54, the molten light impermeable material fills the channels 56 in the rib-mold piece 40 by preferentially melting only through the sections of the baseplate 24 adjacent the channels. This preferential melting occurs because the remainder of the baseplate directly contacts the cool steel of the rib-mold piece 40, and therefore withstands the high temperature of the molten material without melting.

In the regions where the molten light impermeable material melts through the light permeable material of the baseplate, a unitary structure composed of the two materials is formed. However, the discrete molded regions of material are maintained, producing the above-described microplate having a frame and wells with sidewalls made of the light impermeable material, and well bottoms made of a light permeable material having the impermeable ribs extending therethrough. This molding technique creates a strong bond between the dissimilar materials that prevents these materials from peeling apart during use.

Upon cooling, the molten material contracts by approximately 0.05 percent, while the light permeable baseplate does not contract. This contraction has the potential to result in warpage of the finished product, as well as separation of the two materials. However, the nubs 28 provide a mechanical interlock that essentially prevents warpage from occurring. Nubs 28 compensate for warping by providing areas of stress relief during the molding process that allow for changes in the volume of the molten material due to thermal contraction. Thus, the microplate 10 is substantially free from any warping. The nubs further assist in ensuring a strong bond between the two materials. Although some portion of each nub 28 may melt during the molding process, at least some of each nub 28 should remain intact and extend into the impermeable material so that when the molten material cools, the bond is strengthened and the baseplate 24 will not separate from the remainder of the microplate.

The specific temperature and pressure under which the molten impermeable material is injected into the mold varies depending upon the particular material used. The temperature should be sufficiently high so that it exceeds the melting point of both the light impermeable material and the permeable material that forms baseplate 24. Furthermore, the injection pressure should be sufficient to flow the impermeable material into the mold cavity, and to maintain a contact pressure of the impermeable material against the baseplate 24 above channels 56 so that the molten material melts through these areas of the baseplate. However, the temperature and pressure should not be so high that the molten impermeable material flows into the light permeable baseplate in areas other than where the ribs are to be formed, resulting in unusable wells having light impermeable bottoms, or bottoms with a light permeable area that is substantially reduced. The table below provides examples of suitable temperature and pressure ranges for the exemplary materials discussed above.

| Material | Temperature (degrees F.) | Pressure (psi) |
| --- | --- | --- |
| polystyrene | 420–450 | 1200–1500 |
| polyolefin | 420–450 | 1200–1500 |
| polyacrylonitrile | 440–450 | 1200–1600 |
| acrylic | 440–540 | 1200–1600 |
| polyester | 480–550 | 1200–1800 |
| polycarbonate | 550–600 | 1400–2000 |
| polymethylpentene | 500–580 | 1200–1600 |

Figure 8:
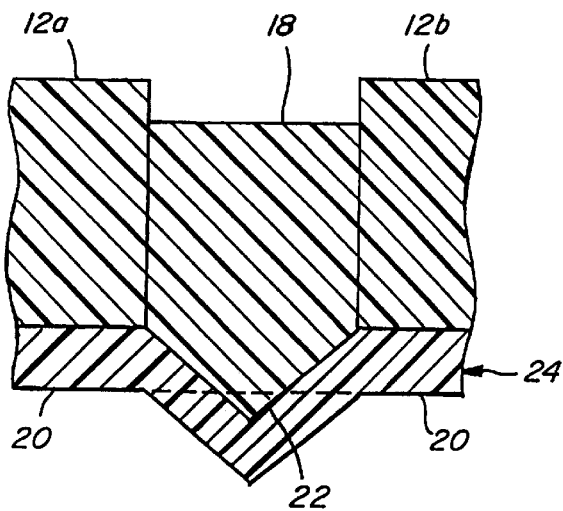
FIG. 8 is a partial cross-sectional view of an alternate embodiment of the microplate of the present invention.

It has been found that when using the above-described method of forming a microplate, the light impermeable material may not always burn entirely through the baseplate 24 to form the ribs 22 described above. Rather, the light impermeable material may at times simply distort the baseplate 24 in the area above the channels 56. FIG. 8 is a partial cross-sectional view of a microplate, such as the one shown in FIGS. 1–2, wherein the light impermeable material has not fully melted through the baseplate 24 between two wells 12*a* and 12*b*. However, the section of the baseplate 24 disposed between wells 12*a* and 12*b* has been distorted by the molten material, which forms a rib 22 between wells 12*a* and 12*b*. As shown in FIG. 8, the baseplate 24 may be distorted so that the section extending between wells 12*a* and 12*b* is offset from the sections that form the bottoms 20 of those adjacent wells, such that no plane passing through the bottoms of both wells 12*a* and 12*b* passes through the entire section of the baseplate extending between the wells. Therefore, no path exists for light to pass between adjacent wells 12*a* and 12*b* through baseplate 24. Furthermore, the light impermeable rib 22 is disposed between the bottoms 20 of wells 12*a* and 12*b* so that any plane passing through the bottom of the both wells intersects rib 22. Thus, there is no sight line between the bottoms of wells 12*a* and 12*b*, and rib 22 prevents any light from passing between the adjacent wells through the light permeable baseplate.

As should be appreciated from the foregoing, both embodiments of the microplate of the present invention (shown in FIGS. 2 and 8) are effective in preventing optical cross-talk between adjacent wells. It should be understood that microplates may be formed that combine these two configurations, with the light impermeable material melting entirely through the baseplate 24 in some areas and distorting the baseplate in others. Thus, in one embodiment of the invention, a microplate is provided that combines these two configurations, each of which is effective in preventing optical cross-talk.

Having thus described several illustrative embodiments of the present invention, various alterations, modifications and improvements may occur to those skilled in the art. Such alterations, modifications and improvements are intended to be within the spirit and scope of the invention. Accordingly, the foregoing description is by way of example only and is not limiting. The invention is limited only by the appended claims and their equivalents.

What is claimed is:

1. A method of making a microplate having a plurality of wells, each of the plurality of wells having light impermeable sidewalls and a light permeable bottom wall, the method comprising the steps of:

(A) inserting a plate of light permeable material into a mold cavity that includes sections shaped to form the sidewalls of the plurality of wells, the plate being positioned adjacent the sections shaped to form the sidewalls of the plurality of wells in a location corresponding to the bottom walls of the plurality of wells;

(B) injecting molten light impermeable material into the mold cavity; and (C) cooling the light impermeable material to form the microplate with the light impermeable material forming the sidewalls of each of the plurality of wells and the plate of light permeable material forming the bottom wall of each of the plurality of wells.

2. The method of making a microplate as recited in claim 1, wherein step (B) includes a step of injecting the molten light impermeable material into the mold cavity at a temperature and pressure sufficient to cause the light impermeable material to penetrate at least partially through the plate of light permeable material.

3. A method of making a microplate having a plurality of wells, each of the plurality of wells having light impermeable sidewalls and a light permeable bottom wall, the method comprising the steps of:

(A) inserting a plate of light permeable material into a mold cavity that includes sections shaped to form the sidewalls of the plurality of wells, the plate being positioned adjacent the sections shaped to form the sidewalls of the plurality of wells in a location corresponding to the bottom walls of the plurality of wells;

(B) injecting molten light impermeable material into the mold cavity; and (C) cooling the light impermeable material to form the microplate with the light impermeable material forming the sidewalls of each of the plurality of wells and the plate of light permeable material forming the bottom wall of each of the plurality of wells;

wherein step (B) includes a step of injecting the molten light impermeable material into the mold cavity at a temperature and pressure sufficient to cause the light impermeable material to penetrate completely through the plate of light permeable material at predetermined locations.

4. The method of making a microplate as recited in claim 3, wherein:

step (A) includes a step of inserting the plate of light permeable material into the mold cavity so that the plate separates the mold cavity into first and second chambers, the mold cavity providing no path for the molten light impermeable material to pass between the first and second chambers other than through the plate of light permeable material.

5. The method of making a microplate as recited in claim 3, wherein:

step (A) includes steps of inserting into the mold cavity a plate of light permeable material that has surface irregularities at the predetermined locations along a first surface, and inserting the plate so that the plate separates the mold cavity into first and second chambers with the first surface of the plate facing the first chamber; and step (B) includes a step of injecting the molten light impermeable material into the first chamber of the mold cavity.

6. The method of making a microplate as recited in claim 3, wherein:

step (A) includes inserting the plate of light permeable material into a mold cavity having an inner surface for receiving the plate, the inner surface including channels corresponding to the predetermined locations so that the inner surface of the mold cavity does not contact the plate of light permeable material at the predetermined locations.

7. The method of making a microplate as recited in claim 3, wherein step (A) includes steps of:

molding the plate of light permeable material; and inserting the molded plate of light impermeable material into the mold cavity.

8. The method of making a microplate as recited in claim 3, wherein step (A) includes a step of inserting into the mold cavity a plate of light permeable material that has surface irregularities at the predetermined locations.

9. The method of making a microplate as recited in claim 8, wherein:

step (A) includes a step of inserting the plate of light permeable material into a mold cavity having an inner surface for receiving the plate, the inner surface including channels corresponding to the predetermined locations so that the inner surface of the mold cavity does not contact the plate of light permeable material at the predetermined locations.

10. The method of making a microplate as recited in claim 9, wherein:

step (A) includes a step of inserting the plate of light permeable material into the mold cavity so that the surface irregularities on the plate of light permeable material are aligned with the channels in the inner surface of the mold cavity.

11. The method of making a microplate as recited in claim 9, wherein:

step (A) includes a step of inserting the plate of light permeable material into the mold cavity so that the plate separates the mold cavity into first and second chambers, the mold cavity providing no path for the molten light impenneable material to pass between the first and second chambers other than through the plate of light permeable material.

12. The method of making a microplate as recited in claim 11, wherein:

step (A) includes steps of inserting the plate of light perrmeable material into the mold cavity so that the surface irregularities face the first chamber; and step (B) includes a step of injecting the molten light impermeable material into the first chamber of the mold cavity.

13. The method of making a microplate as recited in claim 3, wherein:

step (A) includes a step of inserting the plate of light permeable material into a mold cavity having a surface for receiving the plate, the surface including channels corresponding to the predetermined locations so that the inner surface of the mold cavity does not contact the plate of light permeable material at the predetermined locations; and step (B) includes a step of injecting the molten light impermeable material into the mold cavity so that the molten material fills the channels in the mold cavity surface.

14. The method of making a microplate as recited in claim 13, wherein:

step (A) includes a step of inserting the plate of light permeable material into a mold cavity wherein the channels on the inner surface of the mold include at least one channel disposed between sections of the mold shaped to form the sidewalls of adjacent wells, so that the molten material that fills the at least one channel forms a rib disposed between the first and second wells to prevent light from passing therebetween through the plate of light permeable material.

15. The method of making a microplate as recited in claim 13, wherein:

step (A) includes a step of inserting the plate of light permeable material into a mold cavity wherein the channels on the inner surface of the mold are disposed between sections of the mold shaped to form the sidewalls of adjacent wells, so that the molten material that fills the channels forms a plurality of ribs that separates the layer of light permeable material into a plurality of compartments with each of the plurality of compartments including the bottom of a single one of the plurality of wells.

16. The method of making a microplate as recited in claim 13, wherein:

step (B) includes a step of injecting a light impermeable material that includes a plastic selected from the group consisting of polystyrene, polyacrylonitrile, polycarbonate, polyolefin, polyester, polymethylpentene, and acrylic, and at least one pigment selected from the group consisting of titanium dioxide, zinc oxide, zinc sulfide, carbon black and thiopene.

17. The method of making a microplate as recited in claim 16, wherein:

step (A) includes a step of inserting a plate of a light permeable material selected from the group consisting of polystyrene, polyacrylonitrile, polycarbonate, polyolefin, polyester, polymethylpentene, and acrylic.

* * * * *